United States Patent [19]
Pathak et al.

[11] Patent Number: 5,714,353
[45] Date of Patent: Feb. 3, 1998

[54] SAFE VECTORS FOR GENE THERAPY

[75] Inventors: Vinay K. Pathak; Wei-Shau Hu, both of Morgantown, W. Va.

[73] Assignee: Research Corporation Technologies, Inc., Tucson, Ariz.

[21] Appl. No.: 248,132

[22] Filed: May 24, 1994

[51] Int. Cl.$^6$ .......................... C12N 15/64; C12N 15/79; C12N 1/20; C12N 5/10

[52] U.S. Cl. .................. 435/91.42; 435/235.1; 435/252.1; 435/320.1; 435/325; 435/172.3

[58] Field of Search ................... 435/172.3, 320.1, 435/91.42, 235.1, 252.1, 325; 536/23.1, 23.7, 23.72; 935/23, 24, 32, 57, 70

[56] References Cited

U.S. PATENT DOCUMENTS

| | | | |
|---|---|---|---|
| 4,861,719 | 8/1989 | Miller | 435/236 |
| 4,980,289 | 12/1990 | Temin et al. | 435/235.1 |

FOREIGN PATENT DOCUMENTS

| | | |
|---|---|---|
| WO 93/17118 | 9/1993 | WIPO |
| WO 94/03622 | 2/1994 | WIPO |

OTHER PUBLICATIONS

Emerman et al. (1984) "High–Frequency Deletion in Recovered Retrovirus Vectors Containing Exogenous DNA with Promoters" *J. Virol.* 50:42–49.

Yamada et al. (1992) "Retrovirus–Mediated Gene Transfer Targeted to Malignant Glioma Cells in Murine Brain" *Jpn. J. Cancer Res.* 83:1244–1247.

Boris–Lawrie et al. (1994) "The Retroviral Vector" in *Annals New York Academy of Sciences*, 59–71.

Julias et al. (1995) "E Vectors" Development of Novel Self–Inactivating and Self–Activating Retroviral Vectors for Safer Gene Therapy *J. Virol.* 69:6839–6846.

Blaese et al. (1993) "Strategies for Gene Therapy" *Pathologie Biologie* 41(8):672–676.

Kubota et al. (1993) "Long Cellular Repeats Flanking a Defective HTLV–I Provirus: Implication for Site–Targeted Integration" *Science* 8:2873–2877.

Mulligan, R. C. (1993) "The Basic Science of Gene Therapy" *Science* 260: 926–932.

Freeman et al. (1993) "Clinical Trials of Gene Therapy" *Advanced Drug Delivery Reviews* 12:169–183.

Salmons et al. (1993) "Targeting of Retroviral Vectors for Gene Therapy" *Human Gene Therapy* 4:129–141.

Morgan et al. (1993) "Advances in Recombinant Retroviruses for Gene Delivery" *Advanced Drug Delivery Reviews* 12:143–158.

Culver et al. (1992) "In Vitro Gene Transfer with Retroviral Bector–Producer Cells for Treatment of Experimental Brain Tumors" *Science* 256: 1550–1552.

Ezzeddine et al. (1991) "Selective Killing of Glioma Cells in Culture and in Vivo by Retrovirus Transfer of the Herpes Simplex Virus Thymidine Kinase Gene" *The New Biologies* 3: 608–614.

Moolten et al. (1990) "Curability of Tumors Bearing Herpes Thymidine Kinase Genes Transferred by Retroviral Vectors" *Journal of National Cancer Institute* 82:297–300.

(List continued on next page.)

*Primary Examiner*—James Ketter
*Assistant Examiner*—Robert Schwartzman
*Attorney, Agent, or Firm*—Scully, Scott, Murphy & Presser

[57] ABSTRACT

The present invention provides retroviral vectors comprising direct repeats flanking a sequence that is desired to be deleted upon reverse transcription in a host cell. In a preferred embodiment the sequence that is desired to be deleted is the retroviral cis-acting encapsidation sequence (E) essential for virus production in helper cells. In gene therapy embodiments, the E sequence is deleted upon reverse transcription in target cells, thus preventing spread of retroviral vectors to non-target cells in the event of infection with replication competent viruses. The retroviral vectors of the present invention thus provide safe vectors for gene therapy.

35 Claims, 5 Drawing Sheets

OTHER PUBLICATIONS

Short et al. (1990) "Gene Delivery to Glioma Cells in Rat Brain by Grafting of a Retrovirus Packaging Cell Line" *J. of Neuroscience Research* 27:427–439.

Takamiya et al. (1992) "Gene Therapy of Malignant Brain Tumors: A Rat Glioma Line Bearing the Herpes Simplex Virus Typle 1–Thymidine Kinase Gene and Wild Type Retrovirus Kills Other Tumor Cells" *J. of Neuroscience Research* 33:493–503.

Ram et al. (1993) "In Situ Retroviral–Mediated Gene Transfer for the Treatment of Brain Tumors in Rats" *Cancer Research* 53:83–88.

Marshall, E. (1995) "Gene Therapy's Growing Pains" *Science* 269:1050–1055.

Brown, D. (1995) "Gene Therapy Oversold by Researchers, Journalists" *The Washington Post:* A1 & A22.

Coghlan, H. (1995) "Gene Dream Fades Away" *New Scientist:* 14–15.

Rhode et al. (1987) "Instability of Large Direct Repeats in Retrovirus Vectors" *J. of Virol.* 61(3):925–927.

Boris–Lawrie et al. (1993) "Recent Advances in Retrovirus Vector Technology", *Current Opinion in Genetics and Development* 3, 102–109.

Pathak et al. (1990) "Broad Spectrum of in vivo Forward Mutations, Hypermutations and Mutational Hotspots in a Retroviral Shuttle Vector after a Single Replication Cycle: Substitutions, Frameshifts and Hypermutations", *Proc. Natl. Acad. Sci. USA* 87, 6019–6023.

Pathak et al. (1990) "Broad Spectrum of in vivo Forward Mutations, Hypermutations and Mutational Hotspots in a Retroviral Shuttle Vector after a Single Replication Cycle: Deletions and Deletions with Insertions", *Proc. Natl. Acad. Sci. USA* 87, 6024–6028.

Watt et al. (1993) "A Review of Gene Transfer Techniques", *The American Journal of Surgery* 165, 350–354.

Jones et al. (1994) "One Retroviral RNA is Sufficient for Synthesis of viral DNA" *J. Virol.* 68:207–216.

Yan et al. (1994) "A double hairpin structure is necessary for the efficient encapsidation of spleen necrosis virus retroviral DNA" *Embo J.* 13:713–726.

Transfect

DSDH helper cells (G418 selection)

Harvest virus

Infect D17 cells (G418 selection)

Recover proviruses

SAFE VECTORS FOR GENE THERAPY

This invention was made with United States government support under grant 5R29CA58875-02 awarded by the National Institutes of Health. The United States government has certain rights in the invention.

FIELD OF THE INVENTION

Retroviral vectors provide an efficient means for introducing new genetic information into mammalian cells. Although retroviral vectors are designed to be replication defective, there is nonetheless the risk in gene therapy applications that the unintended presence of a replication competent virus can result in viral replication in the host. The present invention overcomes this safety concern by providing retroviral vectors containing direct repeats flanking the cisacting encapsidation sequence (E) essential for virus production in helper cells. The E sequence is deleted upon reverse transcription in target cells, thus preventing spread of retroviral vectors to non-target cells in the event of infection with replication competent viruses. Another safety feature of the present invention is that the E-vectors are likely to reduce the probability of wildtype virus generation by recombination in the helper cells. With the retroviral vectors of the prior art, replication competent virus can be formed in the helper cells through recombination events between the viral protein encoding genes in the helper cell and the retroviral vector. Because E is deleted at a high frequency in these vectors, the recombination events leading to generation of replication competent virus is less likely. The retroviral vectors of the present invention thus provide safe vectors for gene therapy.

BACKGROUND OF THE INVENTION

Retroviruses are RNA viruses that replicate through a double-stranded DNA intermediate. After a retrovirus infects a host cell, the retroviral genomic RNA is reverse transcribed to the double stranded DNA form. This DNA can integrate into the host genome to form a provirus. Reverse transcription requires cis-acting viral sequences including the primer binding site (pbs), the repeat (R) region of the long terminal repeats (LTRs), and the polypurine tract (ppt). Viral terminal attachment sites (att) mediate the integration of the provirus into the host genome. The integrated provirus is transcribed into full-length and spliced mRNA. These RNAs are used as templates to translate viral proteins. Full length mRNA is packaged by the viral proteins, which recognize viral RNA by the cis-acting E sequence. The viral particles, or virions, exit the cell by budding from the cell membrane.

Retroviral vectors containing parts of the retrovirus are used to introduce foreign DNA into eukaryotic cells. Retroviral vectors usually contain the cis-acting sequences required for packaging, reverse transcription, and integration. However, these vectors are replication incompetent because they are defective in retroviral structural genes. Helper cells containing helper virus DNA supply the deficient viral gene products. Thus by transfecting the replication incompetent retrovirus into helper cells, retroviral RNA can be packaged and released as vector virus particles. Because the helper virus is deficient in cis-acting functions, its RNA is not packaged, and helper-free viral stocks can be produced. The released vector-containing particles can be used to introduce the foreign DNA into target cells.

A safety concern with regard to the use of retroviral vectors for gene therapy is raised by the possibility that an endogenous retrovirus could act as a helper virus. This would result in the replication of the retroviral vector containing the therapeutic gene, and its spread to non-target cells. In addition, replication competent virus can be generated by recombination between sequences of the retroviral vector and the helper virus. Attempts in the prior art to address this safety concern include redesign of helper cell lines to contain minimum sequence overlap with the retroviral vector (Boris-Lawrie and Temin, 1993, *Current Opinion in Genetics and Development* 3:102) and the construction of promoter deficient retroviral vectors (U.S. Pat. No. 4,980,289 to Temin et al.).

The present invention represents a novel approach to the resolution of this safety issue by providing retroviral vectors that autoinactivate by deleting the cis-acting encapsidation sequence upon reverse transcription in target cells.

Retroviral genomes are subject to frequent mutation, including substitutions, hypermutations, frameshifts and deletions. Using a spleen necrosis virus (SNV)-based retroviral vector, Pathak and Temin (1990, *Proc. Natl. Acad. Sci.* 87:6019) identified a broad spectrum of mutations, hypermutations and mutational hotspots, including direct repeats. In vectors having two adjacent 110-nucleotide repeats, a deletion of one direct repeat occurred in 41% of the proviral clones. Pathak and Temin (1990, *Proc. Natl. Acad. Sci.* 87:6024) suggest that some mutations are caused by the low processivity of the reverse transcriptase, resulting in template misalignment.

In accordance with the present invention it has been discovered that the low processivity of the reverse transcriptase can be manipulated to provide vectors in which specific sequences are selectively deleted upon replication in a target cell. The selective deletion of a sequence that has been inserted within a coding region or regulatory sequence allows the reconstitution and activation of that sequence. This discovery of selective deletion has also led to the discovery of retroviral vectors in which a particular sequence, for example the cis-acting E-sequence, is retained for viral production in helper cells, but deleted subsequent to infection of target cells. The subject retroviral vectors thus overcome a deficiency of known retroviral vectors for gene therapy.

SUMMARY OF THE INVENTION

The present invention is directed to a retroviral vector comprising the cis-acting retroviral sequences required for packaging, reverse transcription, and integration, and direct repeats flanking a sequence that is desired to be deleted upon reverse transcription in a target cell. In another embodiment the retroviral vector further comprises a restriction endonuclease recognition site for insertion of a non-retroviral sequence. In another embodiment the retroviral vector further comprises a non-retroviral sequence. In a preferred embodiment the non-retroviral sequence is the coding region of a polypeptide or protein useful in gene therapy, and the coding region is under the control of the retroviral promoter or non-retroviral promoter. In another preferred embodiment the sequence that is desired to be deleted is the retroviral encapsidation sequence.

In another aspect of the invention, host cells containing the vector of the invention are provided.

A further aspect of the present invention is directed to virions produced from the retroviral vector of the invention.

The present invention further provides a kit containing the retroviral vector of the present invention, and a pharmaceutical composition comprising the vectors, virions or helper cells transfected by the vector of the present invention.

The present invention is also directed to a method of deleting a viral sequence, such as the encapsidation sequence, or a non-viral sequence from a retrovirus. A method of activating a gene function by deletion of an insertional inactivator is a further aspect of the present invention.

A method of gene therapy comprising providing the vectors, virions or helper cells transfected by the vectors of the present invention to a target cell is also provided.

DETAILED DESCRIPTION OF THE INVENTION

Figure 1:
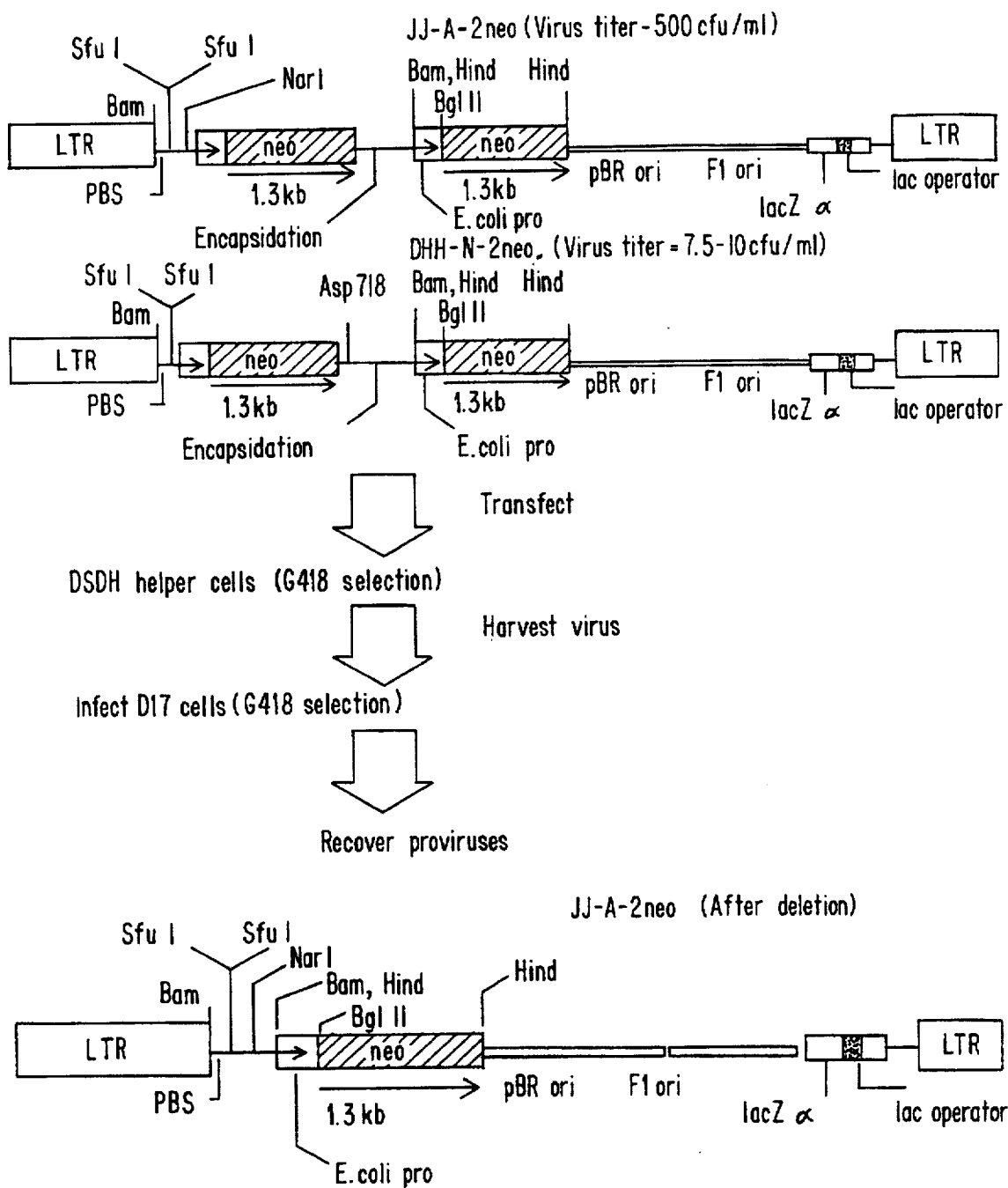
FIG. 1 provides diagrams of the spleen necrosis virus (SNV)-based shuttle vectors JJ-A2neo and DHH-N2neo, a protocol for the production of provirus, and a diagram of JJ-A-2neo after deletion of the encapsidation sequence.

The present invention relates to retroviral vectors comprising the cis-acting retroviral sequences required for packaging, reverse transcription, and integration, and direct repeats flanking a sequence that is desired to be deleted upon reverse transcription in a host cell. It has been discovered in accordance with the present invention that the subject retroviral vectors can be transfected into helper cells from which recombinant retrovirus can be produced. Virions containing the recombinant retrovirus are used to infect target cells. When the retroviral RNA is reverse transcribed in the target cell, the upstream (5') copy of the direct repeat and the sequence between the direct repeats are deleted. High efficiency deletion can be achieved.

In a preferred embodiment, the sequence flanked by the direct repeats is the cis-acting retroviral encapsidation (E) sequence. The E sequence is retained when the vector is transfected into helper cells, where the E sequence is essential for the production of the recombinant retrovirus. However, when target cells are infected with the recombinant retrovirus, reverse transcription results in the production of proviral DNA from which the 5' direct repeat and the E sequence have been deleted. The proviral DNA is transcribed to provide RNA, but the RNA cannot be packaged into infectious virus particles due to the deletion of the E sequence. Accordingly, the retroviral vectors of the present invention in which the E sequence is flanked by direct repeats are "self-inactivating retroviral vectors".

Because cis-acting E sequences can be deleted at high efficiency during reverse transcription in the target cell, infectious viral particles derived from the retroviral vector cannot be produced, even in the event of infection with replication competent virus. Thus the retroviral vectors of the present invention overcome a safety concern of gene transfer, that is the spread of retroviral vectors from target to non-target cells. Another safety feature of the subject retroviral vectors is the reduced probability of generation of replication competent virus by recombination.

The retroviral vectors of the invention comprise the cis-acting retroviral sequences required for packaging, reverse transcription, and integration, and direct repeats flanking a sequence that is desired to be deleted upon reverse transcription in a host cell. In another embodiment, the retroviral vectors further comprise a restriction endonuclease recognition site. In a further embodiment, the retroviral vectors further comprise a non-retroviral sequence.

The cis-acting retroviral sequences can be derived from a retrovirus or can be synthesized by methods known to one of ordinary skill in the art based upon the known sequences of retroviruses. The ordinarily skilled artisan is aware of the essential cis-acting retroviral sequences, which are present in most currently used retroviral vectors and are reviewed by Boris-Lawrie and Temin, 1993, *Current Opinion in Genetics and Development* 3:102. Cis-acting sequences required for reverse transcription include the primer binding site (pbs), the repeat (R) region of the long terminal repeats (LTRs), and the polypurine tract (ppt). Cis-acting sequences required for integration of the viral DNA into the host genome are the terminal attachment sites (att). The cis-acting E sequence, or packaging sequence, is generally located between the unique 5' (U5) region of the LTR and the beginning of gag. E sequences have been defined for numerous retroviruses, including murine leukemia virus (MLV) (Bender et al., 1987, *J. Virol.* 61:1639), human immunodeficiency virus type 1 (Lever et al., 1989, *J. Virol.* 62, 4085; Watanabe et al., 1982, *Proc. Natl. Acad. Sci.* 79: 5986), avian leukosis virus (Watanabe et al., 1982), Mason-Pfizer monkey virus (MPMV) (International Patent Application PCT/GB93/01620) and spleen necrosis virus (SNV) (Watanabe et al., 1982).

Direct repeats are defined herein as a pair of homologous sequences of from about 50 to about 100% identity. In a preferred embodiment the direct repeats consist of ten to twenty base pairs of 100% identity within a repeat of overall identity of 50–100%. In another preferred embodiment the direct repeats are a pair of sequences of from about 75% to about 100% identity. In a most preferred embodiment the pairs are 100% identical.

The selection of sequences to provide the direct repeats in the retroviral vectors of the present invention is a matter of design choice by the ordinarily skilled artisan. In a preferred embodiment the size of the direct repeats is from about 300 to about 2000 base pairs although larger and smaller direct repeats are also contemplated in accordance with the invention. The ordinarily skilled artisan can determine repeats of appropriate size and identity by transfecting helper cells with the retroviral vector, harvesting virus, infecting permissive target cells with the virus, and recovering and characterizing proviral DNA. The proviral DNA can be characterized for example by sequencing or by restriction analysis to determine whether one repeat and the intervening sequence have been deleted. In a more preferred embodiment the size of the direct repeats is from about 300 base pairs to about 1300 base pairs. In a particularly preferred embodiment the size of the direct repeats is about 1300 base pairs, and efficiency of deletion of one direct repeat and the sequence flanked by the repeats is approximately 100%. An efficiency of deletion of approximately 100% is preferred, particularly in embodiments in which the sequence to be deleted is the E-sequence and the vectors are intended for use in gene therapy. However, in certain embodiments in which an additional selection step is employed, efficiencies of deletion of as low as 25–40% are acceptable. An additional selection step can be employed, for example, if the direct repeats can be selected such that a functional selectable marker gene is reconstituted by the deletion of one repeat and the sequence flanked by the repeat. Selectable marker genes such as neo can be used for the selection step. The neogene encodes neomycin phosphotransferase which confers resistance to the neomycin analog G418. For example, a vector can be constructed which contains the first two-thirds of the neogene (ne) upstream (5') of the E sequence and the last two-thirds of neo (eo) downstream (2') of the E sequence. The middle one-third of neo (e) is thus the direct repeat and the upstream direct repeat (e) and any sequence between the direct repeats (E) provides an insertional inactivator to a functional neogene. Upon reverse transcription, the first copy of the middle onethird of neo as well as the E-sequence are deleted, resulting in the reconstitution of a functional neo gene. Selection for neomycin resistance thus insures deletion of the E sequence from 100% of the proviruses.

By permitting the reconstitution of a functional gene or regulatory sequence, the retroviral vectors of the present invention are also "self-activating" vectors. In addition to the reconstitution of a selectable marker gene useful in monitoring deletion efficiency, the reconstitution of other genes is contemplated in accordance with the present invention. Reconstitution of a functional coding sequence of a gene product useful in gene therapy is particularly preferred. Another preferred embodiment is the reconstitution of a toxin that can be directed, for example, to a tumor site, or can kill a target cell upon its activation by reconstitution in the target cell. Reconstitution of a functional gene is a particularly useful embodiment because the gene is only rendered active upon infection of the target cell by the deletion of the sequence between the direct repeats.

The sequence between the direct repeats may be any sequence that is desired to be deleted. In a preferred embodiment, the sequence to be deleted is the E sequence. In another preferred embodiment the sequence, along with the upstream direct repeat, provides an insertional inactivator, the deletion of which results in the reconstitution of a functional gene. The size of the sequence to be deleted is limited by the size limit for insertion of foreign sequences into retroviral vectors, which is about 8 to 10 kilobases (Boris-Lawrie and Temin, 1993). Increasing the size of the sequence to be deleted may reduce efficiency of deletion, and the ordinarily skilled artisan can easily adjust the size of the insertion to achieve the desired efficiency of deletion. For clinical applications, a second selection step may be used as described hereinabove to insure 100% deletion. The ordinarily skilled artisan can measure the efficiency of deletion by recovering proviral DNA from infected cells, and characterizing the proviral plasmids by restriction analysis.

The retroviral vectors of the present invention also comprise a non-retroviral sequence or at least one restriction site for the insertion of a non-retroviral sequence. The non-retroviral sequence allows the expression of genes for recombinant protein production, gene therapy, and disease treatment. The non-retroviral gene may be under the control of the retroviral vector promoter, or a non-retroviral promoter may be introduced into the vector to direct the expression of the nonretroviral gene. The inclusion of more than one transcription unit is contemplated, as is the inclusion of regulatory sequences such as enhancers or internal ribosome entry sites (IRES) to direct translation of LTR-driven polycistronic RNA. Restriction sites are recognition sites for cleavage by restriction endonucleases, and are well known to the ordinarily skilled artisan.

In a preferred embodiment, the non-retroviral sequence encodes a biologically functional protein, i.e. a polypeptide or protein which affects the cellular mechanism of a cell in which the biologically functional protein is expressed. For example, the biologically functional protein can be a protein which is essential for normal growth of the cell or for maintaining the health of a mammal. The biologically functional protein can also be a protein which improves the health of a mammal by either supplying a missing protein, by providing increased quantities of a protein which is under-produced in the mammal or by providing a protein which inhibits or counteracts an undesired molecule which may be present in the mammal. The biologically functional protein can also be a protein which is a useful protein for investigative studies for developing new gene therapies or for studying cellular mechanisms.

The biologically functional protein can be a protein which is essential for normal growth or repair of the human body. The biologically functional protein may also be one which is useful in fighting diseases such as cancer, atherosclerosis, sickle-cell anemia and the thalassemias. Examples of such biologically functional proteins are hemoglobin ($\alpha$, $\beta$ or $\delta$-globin), hematopoietic growth factors such as granulocytemacrophage colony stimulating factor (GM-CSF), macrophage colony stimulating factor (M-CSF), granulocyte colony stimulating factor (G-CSF) and erythropoietin (EPO). Another example is tumor necrosis factor (TNF), which is a molecule that can be used to treat cancer, and in particular, tumors. The tumor suppressor p53 and retinoblastoma (RB) are also contemplated. Various cytokines such as mast cell growth factor (MGF) and interleukins 1–11 are also proteins which are contemplated by the present invention. A multidrug resistance gene (mdR) encoding p-glycoprotein is also contemplated as the nonretroviral sequence. The biologically functional protein may also be a selectable marker for antibiotic resistance in eukaryotes. Other types of selectable markers such as adenine phosphoribosyl transferase (APRT) in APRT-deficient cells, or the firefly luciferase gene are also included. The biologically functional protein can be a protein that will provide the host with an additional or altered enzymatic activity, such as the herpes simplex virus thymidine kinase protein, or a toxin, such as the diphtheria toxin protein. The genes encoding these proteins can be provided by any of a variety of methods, such as routine cloning procedures (Sambrook et al. (1989), *Molecular Cloning: A Laboratory Manual*, Cold Spring Harbor, N.Y.), excision from a vector containing the gene of interest, or chemical or enzymatic synthesis based on published sequence information. In many instances the DNA encoding the protein of interest is commercially available.

In another embodiment the non-retroviral sequence encodes a non-biologically functional protein, for example a toxin or a selectable marker.

In another preferred embodiment the non-retroviral sequence is capable of being transcribed into an RNA molecule which is sufficiently complementary to hybridize to an mRNA or DNA of interest. Such an RNA molecule is hereinafter referred to as antisense RNA, and has utility in preventing or limiting the expression of over-produced, defective or otherwise undesirable molecules. The vector of the present invention can comprise, as the non-retroviral sequence, a sequence encoding an antisense RNA which is sufficiently complementary to a target sequence such that it binds to the target sequence. For example, the target sequence can be part of the mRNA encoding a polypeptide such that it binds to and prevents translation of mRNA encoding the polypeptide. In another embodiment, the target sequence is a segment of a gene that is essential for transcription such that the antisense RNA binds the segment (e.g. a promoter or coding region) and prevents or limits transcription. Hence, the antisense RNA must be of sufficient length and complementarily to prevent translation of its target mRNA or transcription of its target DNA.

In a preferred embodiment the antisense RNA is a 15mer and exhibits 100% complementarily to the target sequence. One of ordinary skill in the art can determine longer or shorter antisense molecules having sufficient complementarily to a target sequence such that the antisense molecule is capable of binding to the target and thereby inhibiting translation or transcription. The non-retroviral sequence can be provided, for example, by chemical or enzymatic synthesis, or from commercial sources. In another preferred embodiment, the non-retroviral sequence is one that can be transcribed into an RNA that is a ribozyme, that is an RNA having enzymatic activity and specificity towards a targeted sequence. Sequences encoding ribozymes are well-known to one of ordinary skill in the art.

The retroviral vectors of the invention may also contain other sequence elements to facilitate vector propagation and isolation and cloning of proviral DNA. Such elements include for example, selectable marker genes and origins of replication that allow propagation in bacteria. For example, retroviral shuttle vectors that allow propagation in bacteria are particularly contemplated, as are host cells comprising the retroviral vectors of the invention. A host cell is defined herein as any cell into which the retroviral vector of the invention can be introduced by standard methods. Such methods are known to the ordinarily skilled artisan and can be found, for example, in Sambrook et al. (1989). In a preferred embodiment, the host cell is a bacterial cell.

The retroviral vectors of the present invention can be constructed by standard recombinant DNA methods. Standard techniques for the construction of such vectors are well-known to those of ordinary skill in the art and can be found in reference such as Sambrook et al. (1989) or any of the myriad of laboratory manuals on recombinant DNA technology that are widely available. A variety of strategies are available for ligating fragments of DNA, the choice of which depends on the nature of the termini of the DNA fragments and can be readily determined by the skilled artisan.

The retroviral vectors of the present invention are transfected into suitable helper cells by standard methods known to one of ordinary skill in the art. Suitable helper cells are defined herein as cells that contain helper virus sufficient to allow the packaging of RNA transcribed from the retroviral vector and the release of vector virus particles, or virions. Generally the helper virus contains the trans-acting viral sequences but lacks the cis-acting sequences required for packaging. Such helper cells are known and available to one of ordinary skill in the art, and include, for example, C3A2 cells.

Recombinant retrovirus produced from the transfected cells is harvested by standard methods. The harvested retrovirus, in the form of virions, is used to infect a permissive target cell by standard techniques. A target cell is defined herein as any cell that is permissive to infection by the virus produced by the retroviral vector of the present invention. The target cell can be in vivo or ex vivo. Representative target cells include, for example, bone marrow stem cells, hepatocytes, muscle cells, tumor cells and airway epithelial cells. The provirus that is formed in the target cell can then express the transgene, or nonretroviral sequence. Because the provirus contains no cis-acting E sequence, endogenous helper proteins cannot trigger production of an infectious virus from the provirus.

Another aspect of the present invention provides a method of deleting a sequence from a retrovirus. This method comprises transfecting a helper cell with a retroviral vector comprising direct repeats flanking the sequence that is desired to be deleted, harvesting virus produced from the helper cells, and infecting target cells with the virus. In a preferred embodiment the sequence to be deleted is the encapsidation sequence.

The present invention also provides a method of activating a gene function. The method comprises transfecting a helper cell with a retroviral vector comprising direct repeats flanking a sequence that is desired to be deleted wherein the upstream direct repeat and the sequence to be deleted provide an insertional inactivator of a functional gene. Virus is harvested from the helper cells, and target cells are infected with the virus. Reverse transcription in the target cell results in deletion of the insertional inactivator and reconstitution of the gene function.

A method of gene therapy comprising providing a therapeutically effective amount of the vectors, virions or helper cells transfected by the vector of the present invention to a target cell is also provided. In one embodiment, the vector and a suitable helper cell, or the virions containing the retrovirus produced by the retroviral vector of the present invention are used for ex vivo infection of target cells derived from a patient in need of such treatment, followed by replacement of the infected cells into the patient, for example by transplantation or intravenous transfusion or injection. Because these virions contain a retrovirus that is rendered replication incompetent after reverse transcription in the target cell, even in the presence of helper virus, the virions are also useful for safe direct injection into the patient, for example at a tumor site. Thus another embodiment is a method of gene therapy providing a therapeutically effective amount of the virions of the invention to a target cell within a patient in need of such treatment, for example by transfusion or injection. In another embodiment of gene therapy, a therapeutically effective amount of helper cells transfected by the retroviral vector are provided to a target cell in a patient in need of such treatment, for example by injection or transplantation.

The present invention further provides a kit having a container adapted contain the retroviral vector of the present invention.

The present invention further provides a pharmaceutical composition comprising the vectors, virions or helper cells transfected by the vector of the present invention and a pharmaceutically acceptable carrier. As used herein, a pharmaceutically acceptable carrier includes any and all solvents, dispersion media, culture from helper cell media, isotonic agents and the like. The use of such media and agents in pharmaceutical compositions is well known in the art. Except insofar as any conventional media or agent is incompatible with the vectors, virions or helper cells of the present invention, its use in the pharmaceutical compositions is contemplated. Supplementary active ingredients can also be incorporated into the compositions. The pharmaceutical compositions of the present injection may be administered in a convenient manner, including by aerosol inhalation, injection, ingestion, transfusion, implantation or transplantation.

The following examples further illustrate the invention.

EXAMPLE 1

This example demonstrates the construction of retroviral vectors that contain direct repeats flanking the encapsidation sequence.

Two spleen necrosis virus (SNV) based E-retroviral shuttle vectors designated DHH-N-2neo and JJ-A2neo were constructed and are depicted in FIG. 1. DHH-N-2neo and JJ-A2neo contain two full copies of the neomycin resistance gene(neo) flanking the encapsidation sequence. The difference in the two vectors is the placement of the upstream neo. The neo was placed 31 bp further upstream in DHH-N-2neo, to include more of the viral encapsidation sequence. The neogene constitutes a 1323 base pair direct repeat separated by 232 or 256 base pairs containing the E sequence, respectively.

A third E-vector, JJ-Neo-eo (FIG. 2) was constructed and contains one full copy of the neo and the last two-thirds of the neo flanking the encapsidation sequence to determine the rate of deletion of direct repeats of different size. The direct repeat in JJ-Neo-eo is the last two thirds of neo and consists of 800 base pairs.

A fourth vector, JJ-Ne-eo—Ires/hygro (FIG. 3) was constructed which contains the first two-thirds of the neo and the second two-thirds of the neo flanking the encapsidation sequence. The direct repeat of this vector is the 400 base pair middle sequence of the neo. When the deletion occurs during reverse transcription, the encapsidation sequence and one of the repeating copies of the middle of the neo are eliminated, and as a result the neo is regenerated. Selection of the infected cells for G418 resistance, a neomycin analog, only selects cells containing proviruses that have deleted the encapsidation sequence and are no longer packageable.

The vectors also contained a pBR origin of replication for propagation in bacteria, and a lac operator sequence for lac repressor mediated purification and cloning of proviral DNA.

Figure 4:
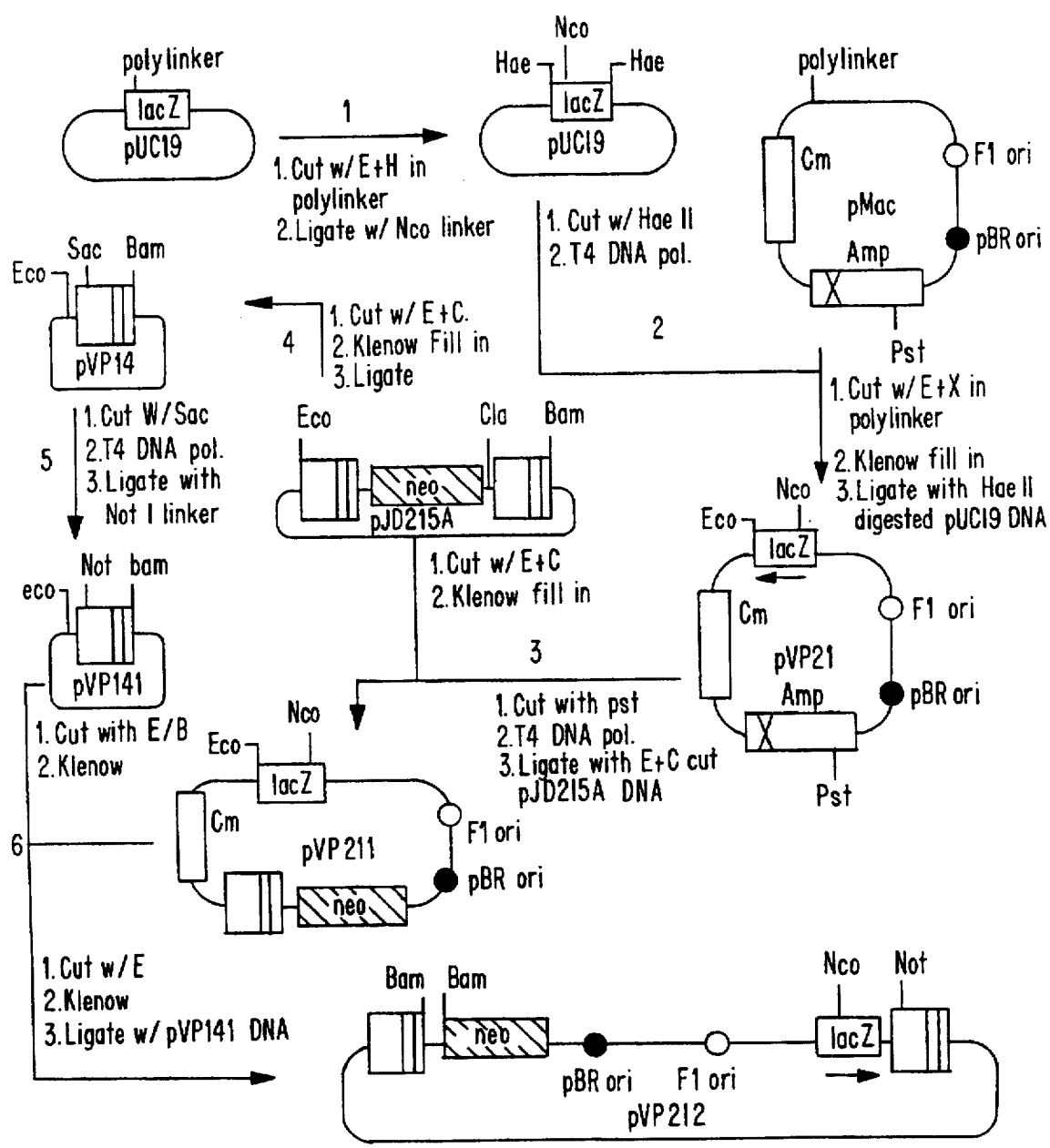
FIG. 4 is a diagram of the construction of retroviral shuttle vector pVP212.

The vectors were constructed as follows. The vectors were derived from retroviral shuttle vector plasmid pVP212, which is known in the art (Pathak and Temin, 1990 Proc. Natl. Acad. Sci. USA 87:6019) and is constructed from fragments of pUC19, pMC and pJD215 as depicted in FIG. 4.

Construction of JJ-A2neo: The VP212 plasmid was digested with Hind III and the 1.3 kb fragment that contained the neogene was purified through gel electrophoresis and a DEAE membrane. The insert was treated with Klenow DNA polymerase. Another aliquot of the VP212 plasmid was digested with Asp 718, treated with Klenow DNA polymerase, and calf intestinal phosphatase. The insert was ligated into the vector with T4 DNA ligase. The structure of the construct was verified by Bgl II restriction enzyme digestions and the new plasmid was named JJ-A2neo (FIG. 1). Construction of the DHH-N-2neo: The VP212 plasmid was digested with Hind III and the 1.3 kb fragment that contained the neo resistance gene was purified as before. A partial digest of JJ19 with Nar I was completed and the linear form of the JJ19 was isolated. The vector and the insert were both treated with Klenow DNA polymerase to generate blunt ends, and the JJ19 vector was treated with calf intestinal phosphatase to dephosphorylate the 5' ends and to prevent self ligation. The insert was ligated into the vector using T4 DNA polymerase. The structure of the construct was verified by BgI II and Xba I restriction enzyme digestions and the new plasmid was named DHH10.

The neogene was isolated from the DHH10 vector using Bam HI restriction endonuclease and gel electrophoresis. The JJ212-E vector was digested with Bam HI to linearize the vector. The linear JJ212-E vector was treated with calf intestinal phosphatase and the neo cassette was ligated into the JJ212-E vector. The resulting plasmid was named DHH-N-2neo (FIG. 1) and contained two neo resistance genes flanking the encapsidation sequence.

Figure 2:
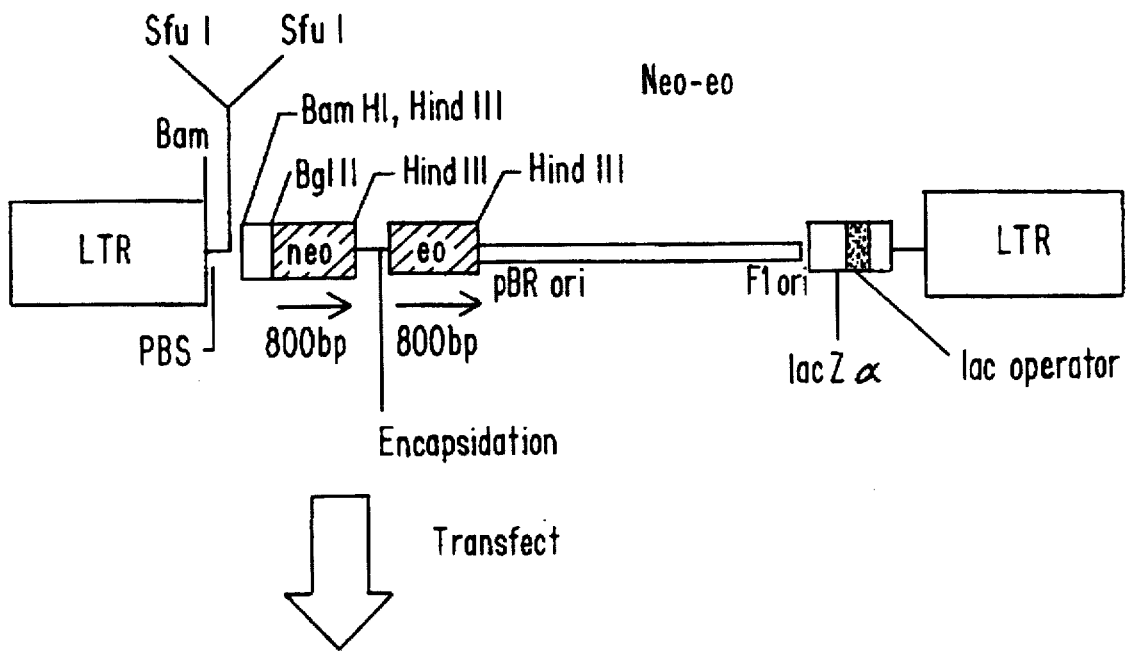
FIG. 2 is a diagram of the SNV-based shuttle vector JJ-Neo-eo, a protocol for the production of provirus, and a diagram of JJ-Neo-eo after deletion of the encapsidation sequence.
Figure 2:
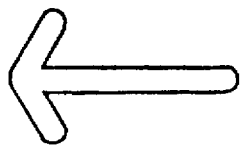
Figure 2:
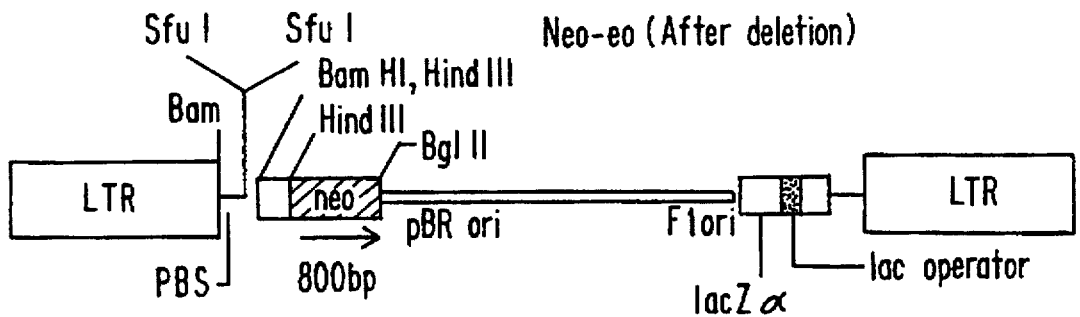

Construction of JJ-Neo-eo vector: The DHH 20 plasmid was digested with Asp 718 and treated with Klenow DNA polymerase and calf intestinal phosphatase. The VP212 plasmid was digested with Hind III and the 1.3 kb fragment was treated with Klenow DNA polymerase. The insert was ligated into the vector with T4 DNA polymerase and the structure of the construct was checked with Bgl II and Hind III restriction enzymes. The new construct was called JJ-Neo-eo (FIG. 2). The plasmid JJ-Neo-eo was deposited in accordance with the Budapest Treaty with the American Type Culture Collection (ATCC), 13201 Parklawn Drive, Rockville, Md., 20852, and has been accorded ATCC Accession Number 97861. Construction of JJ-Ne-eo—Ires/hygro vector: The DHH 20 plasmid was digested with Asp 718 and treated with Klenow DNA polymerase and calf intestinal phosphatase. The VP212 plasmid was digested with Hind III and Nco I and the 800 bp fragment was treated with Klenow DNA polymerase. The insert was ligated into the vector with T4 DNA polymerase and the structure of the construct was checked with Bgl II and Hind III restriction enzymes. The new construct was called Ne-eo.

Figure 3:
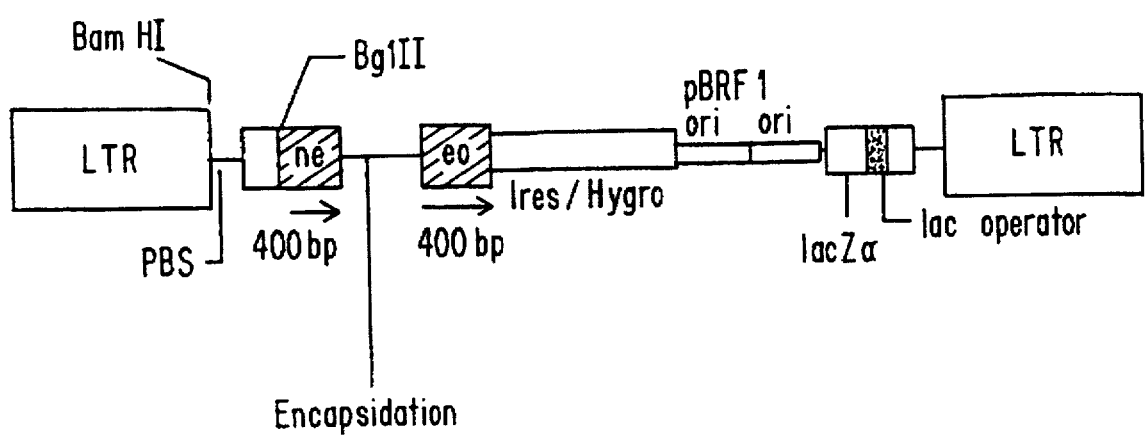
FIG. 3 is a diagram of the SNV-based shuttle vector JJ-Ne-eo—Ires/hygro.

Ne-eo was digested with Hind III, treated with Klenow DNA polymerase to generate blunt ends, and treated with calf intestinal phosphatase to dephosphorylate and prevent self-ligation. MG7, a Bluescript derivative containing the Ires/hygro fragment was digested with Bam HI, and treated with Klenow DNA polymerase. The resulting 1.6 kb fragment was digested with Bam HI, and treated with Klenow DNA polymerase. The resulting 1.6 kb fragment containing the Ires/hygro was gel purified and ligated to the Ne-eo vector to generate JJ-Ne-eo—Ires/hygro (FIG. 3).

Vectors JJ-A2neo and JJ-Ne-eo—Ires/hygro were deposited in accordance with the Budapest Treaty with the American Type Culture Collection, 12301 Parklawn Drive, Rockville Md., 20852, and have been accorded ATCC Accession Numbers 75780 and 75781, respectively.

EXAMPLE 2

This example demonstrates the transfection of mammalian helper cells with the retroviral vectors of Example 1, the harvesting of virus, the infection of permissive cells with the virus, and the recovery and characterization of proviral DNA.

Mammalian Cell Transfection and Virus Infection: VP212, JJ-A2Neo, DHH-N2Neo, JJ-Ne-eo, JJ-Neo-eo and JJ-Ne-eo—Ires/hygro were co-transfected into C3A2 helper cells with a plasmid encoding ouabain resistance (pSVα3.6). A pool of ouabain resistant C3A2 cells were selected, virus was harvested according to standard procedures, and D17 dog cells permissive for SNV infection were infected. Characterization of JJ-A2Neo and DHH-N2Neo: The infected D17 cells were selected for G418 resistance and the virus titers for the Table 1 vectors were determined and are shown in Table 1.

TABLE 1

| Retroviral Vector | Virus Titer/ml (Avg. of 2 experiments) |
|---|---|
| VP212 | 4700 |
| JJ-A2Neo | 1600 |
| DHH-N2Neo | 115 |

These results indicated that insertion of a neo gene in the ASP718 restriction site upstream of the E sequence had little if any effect on the virus replication. In contrast, insertion of the neogene in the Nar I restriction, 31 base pairs upstream of the ASP718 restriction site, significantly reduced virus titers.

From a pool of 2500 G418 resistant colonies obtained from JJ-A2Neo infected cells, approximately 700 proviral DNAs were recovered using the lac repressor protein mediated purification. The proviral DNAs were characterized by restriction mapping analysis to show that 203 of 204 characterized had deleted one neogene and the encapsidation sequence, indicating that the rate of deletion was 99.5%. The JJ-Ne-eo and JJ-Neo-eo vectors were also able to confer G418 resistance to D17 cells efficiently. The proviral DNAs from these vectors has not been characterized.

Figure 5:
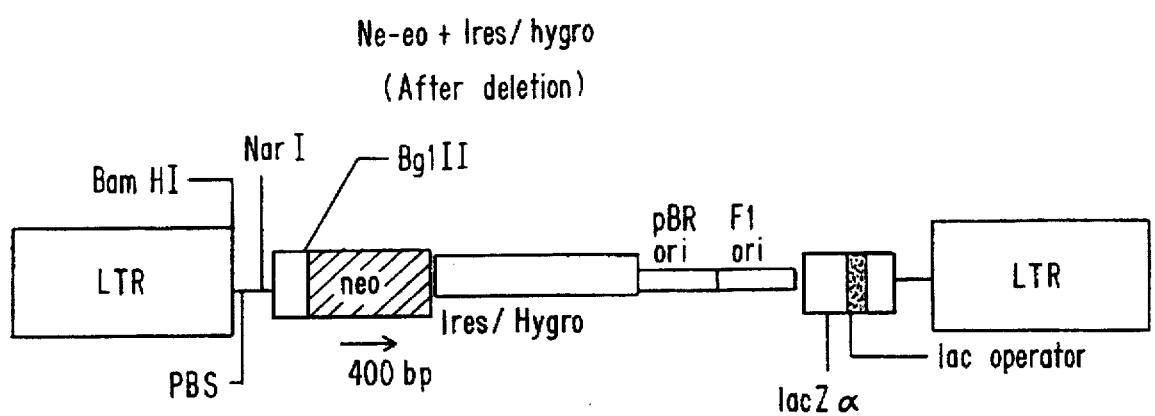
FIG. 5 is a diagram of vector JJ-Ne-eo—Ires/hygro after deletion of the encapsidation sequence.

The structure of JJ-eo -Ires/hygro after deletion is depicted in FIG. 5. Hygro and G418 titers are presented in Table 2.

TABLE 2

| Dilution | Hygro Titer | G418 Titer | G418/Hygro Titer |
|---|---|---|---|
| $10^0$ | TNTC | TNTC | — |
| $10^{-1}$ | $1.9 \times 10^3$/ml | $1.9 \times 10^3$/ml | 0.33 |
| $10^{-2}$ | $1.6 \times 10^3$/ml | $1.6 \times 10^3$/ml | 0.23 |
| AVG | $1.8 \times 10^3$/ml | $1.8 \times 10^3$/ml | 0.28 |

These data indicate that the neomycin gene is reconstituted after one round of virus replication by the deletion of the encapsidation sequence. The frequency of the neo reconstitution/E deletion is approximately 28%.

What is claimed is:

1. A retroviral vector comprising cis-acting retroviral sequences required for packaging, reverse transcription and integration, and direct repeats flanking a sequence that is desired to be deleted upon reverse transcription in a target cell.

2. The retroviral vector of claim 1 which further comprises at least one restriction endonuclease recognition site located at a position outside the direct repeats, for insertion of at least one nucleic acid fraqment.

3. The retroviral vector of claim 1 which further comprises at least one of a non-retroviral sequence encoding a polypeptide or protein, a nonretroviral sequence encoding an antisense RNA, or a nonretroviral sequence encoding a ribozyme.

4. The retroviral vector of claim 1 wherein the sequence that is desired to be deleted is a retroviral encapsidation sequence.

5. The retroviral vector of claim 1 wherein said direct repeats consist of from about 300 to about 2000 base pairs.

6. The retroviral vector of claim 1 wherein the deletion of one direct repeat and the sequence flanked by the direct repeats results in the reconstitution of a coding region of a protein or polypeptide.

7. A host cell comprising the vector of claim 1.

8. A helper cell comprising the retroviral vector of claim 1.

9. A kit comprising the retroviral vector of claim 1.

10. A composition comprising the retroviral vector of claim 1 and a pharmaceutically acceptable carrier.

11. The retroviral vector of claim 1 which further comprises at least one restriction endonuclease recognition site located at a position inside the direct repeats, for insertion of at least one nucleic acid fragment.

12. The retroviral vector of claim 3 wherein the non-retroviral sequence is under the control of a retroviral promoter.

13. The retroviral vector of claim 3 wherein the non-retroviral sequence is under the control of a non-retroviral promoter.

14. The retroviral vector of claim 3 wherein the protein is a biologically functional protein.

15. The retroviral vector of claim 3 wherein the protein is a non-biologically functional protein.

16. The retroviral vector of claim 3 wherein the non-retroviral sequence is transcribed into an antisense RNA upon reverse transcription of the vector in the target cell.

17. The retroviral vector of claim 3 wherein the non-retroviral sequence is transcribed into a ribozyme upon reverse transcription of the vector in the target cell.

18. The retroviral vector of claim 3 wherein transcription of the non-retroviral sequence into an antisense RNA is under the control of a non-retroviral promoter.

19. The retroviral vector of claim 3 wherein transcription of the non-retroviral sequence into a ribozyme is under the control of a non-retroviral promoter.

20. The retroviral vector of claim 5 wherein said direct repeats consist of from about 300 to about 1300 base pairs.

21. The host cell of claim 7 wherein said host cell is a bacterial cell.

22. Virions produced by the helper cell of claim 8.

23. The retroviral vector of claim 20 wherein said direct repeats consist of about 1300 base pairs.

24. A composition comprising the virions of claim 22 and a pharmaceutically acceptable carrier.

25. A recombinant retrovirus comprising an encapsidation sequence flanked by direct repeats.

26. The recombinant retrovirus of claim 25 wherein said direct repeats consist of from about 300 to about 2000 base pairs.

27. The recombinant retrovirus of claim 26 wherein said direct repeats consist of from about 300 to about 1300 base pairs.

28. The recombinant retrovirus of claim 27 wherein said direct repeats consist of about 1300 base pairs.

29. An isolated target cell infected by the retrovirus of any one of claims 25–28.

30. A method of deleting a sequence from a retrovirus which comprises transfecting a helper cell with a retroviral vector comprising said sequence flanked by at least one upstream and at least one downstream direct repeat, harvesting virus produced by said helper cells, and infecting isolated target cells with said virus, wherein upon reverse transcription of the retrovirus in the isolated target cell, the sequence and the upstream direct repeat is deleted.

31. The method of claim 30 wherein said sequence is a retroviral encapsidation sequence.

32. A method of activating a gene function within a retroviral vector which comprises transfecting a helper cell with a retroviral vector comprising at least one upstream and at least one downstream direct repeat fling a sequence that is desired to be deleted, wherein the upstream direct repeat and the sequence to be deleted provide an insertional activator of a functional gene, harvesting virus produced by said helper cells, and infecting isolated target cells with said virus, wherein upon reverse transcription of the retroviral vector in the isolated target cell, the insertional inactivator is deleted thereby activating the gene function within the retroviral vector.

33. Retroviral vector JJ-A-2neo.

34. Retroviral vector JJ-Neo-eo.

35. Retroviral vector JJ-Neo-eo—Ires/hygro.

* * * * *

UNITED STATES PATENT AND TRADEMARK OFFICE
CERTIFICATE OF CORRECTION

PATENT NO. : 5,714,353
DATED : February 3, 1998
INVENTOR(S) : Vinay K. Pathak, et al.

It is certified that error appears in the above-identified patent and that said Letters Patent is hereby corrected as shown below:

On Title Page, Section [56] under "OTHER PUBLICATIONS" Column 2, line 13: "Vitro" should read --Vivo--

Column 5, line 8: "(2')" should read --(3')--

Column 5, line 12: "onethird" should read --one-third--

Column 6, line 21: "δ" should read --γ-- 

Column 8, lines 18: "insertionai" should read --insertional--

Column 10, line 11: "13201" should read --12301--

Column 12, line 53, Claim 32: "fling" should read --flanking--

Column 12, line 65, Claim 35: "Neo" should read --Ne--

Signed and Sealed this

Twenty-ninth Day of February, 2000

Attest:

Q. TODD DICKINSON

Attesting Officer

Commissioner of Patents and Trademarks